(12) United States Patent
Thomas et al.

(10) Patent No.: US 11,013,703 B2
(45) Date of Patent: *May 25, 2021

(54) SOTALOL COMPOSITIONS AND USES OF THE SAME

(71) Applicant: ARBOR PHARMACEUTICALS, LLC, Atlanta, GA (US)

(72) Inventors: H. Greg Thomas, Carrollton, GA (US); Jeffrey S. Kiel, Gainesville, GA (US)

(73) Assignee: Arbor Pharmaceuticals, LLC, Atlanta, GA (US)

(*) Notice: Subject to any disclaimer, the term of this patent is extended or adjusted under 35 U.S.C. 154(b) by 104 days.

This patent is subject to a terminal disclaimer.

(21) Appl. No.: 16/243,440

(22) Filed: Jan. 9, 2019

(65) Prior Publication Data

US 2019/0142772 A1 May 16, 2019

Related U.S. Application Data

(63) Continuation of application No. 15/635,499, filed on Jun. 28, 2017, now Pat. No. 10,206,895, which is a continuation of application No. 14/242,624, filed on Apr. 1, 2014, now Pat. No. 9,724,297.

(51) Int. Cl.
| | |
|---|---|
| *A61K 31/18* | (2006.01) |
| *A61K 9/08* | (2006.01) |
| *A61K 9/00* | (2006.01) |
| *A61K 47/12* | (2006.01) |
| *A61K 47/26* | (2006.01) |
| *A61K 47/02* | (2006.01) |
| *A61K 47/22* | (2006.01) |

(52) U.S. Cl.
CPC ............ *A61K 31/18* (2013.01); *A61K 9/0053* (2013.01); *A61K 9/08* (2013.01); *A61K 47/02* (2013.01); *A61K 47/12* (2013.01); *A61K 47/22* (2013.01); *A61K 47/26* (2013.01)

(58) Field of Classification Search
CPC ........ A61K 31/18; A61K 47/02; A61K 47/12; A61K 47/22; A61K 47/26; A61K 9/0053; A61K 9/08; A61P 9/06; A61P 43/00
See application file for complete search history.

(56) References Cited

U.S. PATENT DOCUMENTS

| | | | |
|---|---|---|---|
| 5,484,776 A * | 1/1996 | Racz | A61K 9/0095 514/54 |
| 9,724,297 B2 * | 8/2017 | Thomas | A61K 9/08 |
| 10,206,895 B2 * | 2/2019 | Thomas | A61K 9/08 |

OTHER PUBLICATIONS

Sharma et al., "Flavouring Agents in Pharmaceutical Formulations", 1988, Ancient Science of Life, vol. 8, Nos. 1, pp. 38-40. (Year: 1988).*
Sidhom et al., "Stability of Sotalol Hydrochloride in Extemporaneously Prepared Oral Suspension Formulations", 2005, Internat. J. Pharmaceutical Compounding, 9(5), pp. 402-406. (Year: 2005).*
Edited by Rowe et al., (2009), "Handbook of Pharmaceutical Excipients (6th ed.)". London: APhA, (PhP) Pharmaceutical Press., pp. 701-707. (Year: 2009).*
Loyd V. Allen, "Stability of Extemporaneously Prepared Oral Liquid Formulations-Part V", 2010, Secundum Artem, 14(3), pp. 1-6. (Year: 2010).*
SOTYLIZE™, Oct. 2014, pp. 1-19. (https://www.accessdata.fda.gov/drugsatfda_docs/label/2014/205108s000lbl.pdf) (Year: 2014).*

* cited by examiner

*Primary Examiner* — My-Chau T. Tran
(74) *Attorney, Agent, or Firm* — King & Spalding

(57) ABSTRACT

The present invention provides oral solutions containing sotalol hydrochloride which advantageously avoid swallowing while providing with improved stability. The present invention also relates to methods of using the oral solutions for treatment of diseases and disorders, such as delay in reoccurrence of atrial fibrillation/atrial flutter and/or ventricular arrhythmias.

19 Claims, No Drawings

SOTALOL COMPOSITIONS AND USES OF THE SAME

FIELD OF THE INVENTION

The present invention relates to pharmaceutical compositions containing sotalol hydrochloride, as well as methods of using such compositions to treat disease or disorders of the heart and methods of preparing such compositions.

BACKGROUND OF THE INVENTION

Sotalol hydrochloride is a non-selective competitive β-adrenergic receptor blocker that also exhibits Class III antiarrhythmic properties by inhibiting potassium channels. Sotalol hydrochloride is currently indicated as a treatment for delay in recurrence of atrial fibrillation/atrial flutter and documented life-threatening ventricular arrhythmias. It is marketed in tablet form as Betapace and Betapace AF.

Some patients, such as children and the elderly, cannot swallow solid dosage forms. In order to provide sotalol hydrochloride to such patients, oral formulations must be prepared extemporaneously, typically at a compounding pharmacy. These oral formulations are suspensions and typically containing 5 mg/mL of sotalol hydrochloride prepared by compounding a Betapace AF tablet and simple syrup. Alternative formulations are suspensions containing 5 mg/mL of sotalol hydrochloride prepared by compounding Betapace with commercially available vehicles including Ora-Plus (which contains microcrystalline cellulose, sodium carboxymethylcellulose, xanthan gum, carageenan, sodium phosphate and citric acid), Ora-Sweet (which contains sucrose, glycerin, sorbitol, citrus-berry flavor, sodium phosphate and citric acid) and Ora-Sweet SF (which contains glycerin, sorbitol, sodium saccharin, xanthan gum, citrus-berry flavor, citric acid and sodium citrate) and are also described in Sidhom, M. B., et al., International Journal of Pharmaceutical Compounding, Vol. 9, No. 5, 2005, pp. 401-406.

Unfortunately, these extemporaneous oral suspensions have limited stability, i.e., only three (3) months when stored at controlled room temperature and ambient humidity.

Accordingly, there remains a need for oral formulations of sotalol hydrochloride suitable for patients that cannot swallow solid dosages that have improved stability suitable for commercial sales.

SUMMARY OF THE INVENTION

The present invention relates to pharmaceutical compositions containing sotalol hydrochloride, as well as methods of using such compositions to treat diseases and disorders of the heart and methods of manufacture. The pharmaceutical compositions of the present invention are oral solutions, which advantageously avoid difficulties in swallowing while offering improved stability.

In a first aspect, the present invention is an oral solution comprising sotalol hydrochloride, wherein the solution is stable for greater than 4 months.

In one embodiment, the oral solution is stable for greater than about 5 months, about 6 months, about 8 months or about 12 months or longer.

In a particular embodiment, the oral solution comprises sotalol hydrochloride and water, and is stable for greater than about 4 months.

In another particular embodiment, the oral solution comprises sotalol hydrochloride and water, and is stable for greater than about 4 months, about 5 months, about 6 moths, about 8 months or about 12 months or longer.

In another embodiment, the oral solution is substantially free of polymers.

In yet another embodiment, the oral solution has an osmolality in the range of about 20 mOsm/kg to about 400 mOsm/kg.

In a still further embodiment, the oral solution has a pH between about 4.5 and about 5.5.

The oral solutions of the present invention may optionally contain additional excipients including buffers, preservatives, flavorings and high potency sweeteners.

In a particular embodiment, the oral solution consists of sotalol hydrochloride, water, citric acid, sodium citrate, sucralose, sodium benzoate and artificial grape flavor.

In another particular embodiment, the oral solution consists of sotalol hydrochloride, water, citric acid, sodium citrate, sucralose, sodium benzoate and artificial grape flavor, and is stable for greater than about 4 months, about 5 months, about 6 moths, about 8 months or about 12 months or longer.

In a second aspect, the present invention is a method of treating a diseases and disorder comprising administering a therapeutically effect amount the oral solution of the present invention to a host in need thereof.

In one embodiment, the disease or disorder is a disease or disorder of the heart.

In a particular embodiment, the disorder is atrial fibrillation/atrial flutter.

In another embodiment, the disorder is a documented life-threatening ventricular arrhythmias.

The therapeutically effective amount may vary, depending on the characteristics of the host and the severity of the disease or disorder. In a particular embodiment, the dose administered depends on the host's creative clearance.

In one embodiment, the host is administered a 80 mg daily dose of the oral solution.

In another embodiment, the host is administered a 160 mg daily dose of the oral solution.

In yet another embodiment, the host is administered a 360 mg daily dose of the oral solution.

In a particular embodiment, administration occurs once, twice or three times a day.

In one embodiment, the host is administered a 80 mg daily dose of the oral solution, once a day.

In another embodiment, the host is administered a 80 mg daily dose of the oral solution, once a day.

DETAILED DESCRIPTION OF THE INVENTION

The present invention relates to pharmaceutical compositions containing sotalol hydrochloride, as well as methods of using such compositions to treat disease and disorders of the heart (i.e., cardiac diseases and disorders), and methods of preparing the same. The pharmaceutical compositions of the present invention are oral solutions and help patients avoid difficulties in swallowing while offering improved stability, particularly over extemporaneously prepared oral suspension of sotalol hydrochloride known in the art.

I. Sotalol Hydrochloride

"Sotalol hydrochloride," as used herein, refers to d,l-N-[4-[1-hydroxy-2-[(1-methylethyl)amino]ethyl]phenyl]methane-sulfonamide monohydrochloride. Both d- and l-isomers have similar Class III antiarrhythmic effects, while the l-isomer is responsible for virtually all of the beta-blocking activity.

II. Pharmaceutical Compositions

The pharmaceutical compositions described herein are solutions, intended for oral administration. The oral solutions of the present invention are intended to provide safe and effective treatment for diseases and disorders, including indications currently treated with the tablet form of sotalol hydrochloride.

The term "solution," as used herein, refers to a homogenous mixture of substances in the liquid phase. More particularly, solutes are dissolved in the solvent (e.g. water) and do not separate out. The solutions of the present invention can be distinguished from suspensions, colloids and dispersions by methods known to those of skill in the art. For example, particulates (solutes) in suspensions will eventually separate (e.g. oil in water). Colloids can be distinguished from solutions using the Tyndall effect.

The pharmaceutical compositions of the present invention are oral solutions comprising sotalol hydrochloride and a solvent, i.e., sotalol hydrochloride dissolved in a solvent. The solvent may vary, and may include purified water, distilled water, saline solution.

In one embodiment, the pharmaceutical composition is an oral solution comprising sotalol hydrochloride and water, to provide an aqueous solution of sotalol hydrochloride.

In one embodiment, the pharmaceutical composition is an aqueous solution comprising sotalol hydrochloride and water, wherein water is present in an amount from about 95% to about 99% by weight, such as, for example, about 95%, about 96%, about 97%, about 98% or about 99%. In a more particular embodiment, water is present in an amount of about 98%.

The pharmaceutical compositions of the present invention have improved stability, particularly compared to the extemporaneously prepared oral suspensions known in the art. The term "stability," as used herein, refers to compliance of the oral solution, at a given time point, with all of the "Shelf-life Specifications" provided in the Examples section. Specifically:

(i) the major (largest) peak in an HPLC trace of the solution should correspond with a sotalol reference standard;
(ii) the UV spectrum of the main peak of the solution should correspond with the a sotalol reference chromatogram;
(iii) sotalol should be present in 90.0% to 110.0% of theoretical, as determined by CTMLP-3056 (analytical method for impurities in sotalol oral solution; measured by HPLC);
(iv) not more than 0.2% related compound A (R,S N[(4-[[(1-methylethyl)amino]acetyl]phenyl]methanesulfonamide monohydrochloride; $C_{12}H_{18}N_2O_3S \cdot HCl$, M.W.=306.81), not more than 0.2% related compound B (R,S N-(4-formylphenyl)methanesulfonamide, $C_8H_9NO_3S$, M.W.=199.23), not more than 0.2% related compound C (R,S N-[4-[2-[(1-methylethyl)amino]ethyl]phenyl]methanesulfonamide monohydrochloride, $C_{12}H_{20}N_2O_2S \cdot HCl$, M.W.=292.83) and not more than 2.5% total impurities;
(v) Sodium benzoate should be present in 80.0% to 110.0% of theoretical, as determined by CTMLP-3057 (analytical assay of sodium benzoate; measured by HPLC);
(vi) The pH is between 4.5 and 5.5;
(vii) Osmolality is less than 400 mOsm/kg; and
(viii) The solution should be a clear, colorless liquid by visual inspection.

The pharmaceutical compositions of the present invention are oral solutions comprising sotalol hydrochloride, stable under varied storage conditions for about 4 months or longer. More particularly, the aqueous oral solutions are stable for greater than about 5 months, greater than about 6 months, greater than about 8 months, greater than about 9 months, greater than about 10 months, greater than about 11 months, greater than about 12 months, greater than about 13 months, greater than about 14 months, greater than about 15 months, greater than about 16 months, greater than about 17 months, greater than about 18 months, greater than about 19 months, greater than about 20 months, greater than about 21 months, greater than about 22 months, greater than about 23 months, greater than about 24 months or greater than about 36 months.

Storage conditions may vary, including by temperature and humidity. Storage may be under acid, neutral and alkaline conditions.

The temperature at which the oral solution is stored may vary. The oral solution is preferably stored at a temperature between about 25° C. and about 40° C. In a particular embodiment, the oral solution is stored at about 25° C. In another particular embodiment, the oral solution is stored at about 30° C. In still another particular embodiment, the oral solution is stored at about 40° C.

The relative humidity (RH) at which the oral solution is stored may vary. The oral solution is preferably stored at an RH of between about 60% and about 75%. In a particular embodiment, the oral solution is stored at about 60% RH. In another embodiment, the oral solution is stored at about 65% RH. In still another particular embodiment, the oral solution is stored at about 75% RH.

In preferred embodiments, the oral solution is stored at a temperature of between about 25° C. and about 40° C. and a RH of between about 60% and about 75% to provide maximum stability over time.

In certain embodiments, the present invention is an oral solution comprising sotalol hydrochloride stable for greater than about four (4) months when stored at about 25° C. and about 60% RH, about 30° C. and about 65% RH or about 40° C. and about 75% RH. In a particular embodiment, the oral solution is stable for about five months, about six months, about seven months, about eight months, about nine months, about ten months, or about eleven months or longer.

In exemplary embodiments, the oral solution of the present invention is about 5%, about 10%, about 15%, about 20%, about 25%, about 30%, about 35%, about 40%, about 45%, about 50%, about 60%, about 65%, about 70%, about 75%, about 80%, about 90%, about 95%, about 100% or more stable than an oral suspension of sodium hydrochloride under the same storage conditions.

The amount of sotalol hydrochloride may vary. In one embodiment, sotalol hydrochloride is present in the oral solution in an amount from about 2 mg/mL to about 8 mg/mL, such as, for example, about 2 mg/mL, about 3 mg/mL, about 4 mg/mL, about 5 mg/mL, about 6 mg/mL, about 7 mg/mL or about 8 mg/mL.

In a particular embodiment, the pharmaceutical composition is an oral solution comprising about 5 mg/ml of sotalol hydrochloride.

Sotalol hydrochloride can be present in the oral solutions of the present invention in an amount from about 0.2% to about 0.8% by weight, such as, for example, about 0.2%, about 0.3%, about 0.4%, about 0.5%, about 0.6%, about 0.7% or about 0.8%.

In a particular embodiment, the pharmaceutical composition is an oral solution comprising about 0.5% by weight sotalol hydrochloride.

In certain embodiments, the pharmaceutical composition of the present invention is an oral solution of sotalol hydrochloride that does not contain polymers, or more particularly, does not contain polymers that contribute to stabilization or emulsification, for example polysaccharide polymers. In an exemplary embodiment, the pharmaceutical composition is an oral solution of sotalol hydrochloride that does not contain polysaccharide polymers, such as xanthan gum.

The osmolality of the oral solution may vary. In one embodiment, the oral solution has an osmolality in the range of about 20 mOsm/kg to about 400 mOsm/kg, such as, for example, from about 50 to about 300 mOsm/kg, from about 100 to about 200 mOsm/kg, from about 50 to about 100 mOsm/kg or about 200 to about 350 mOsm/kg. In a particular embodiment, the osmolality of the oral solution is from about 200 to about 300 mOsm/kg, more particularly from about 200 to about 250 mOsm/kg.

The pH of the oral solutions may range from about 3 to about 7 and provide osmolalities in the range of about 20 mOsm/kg to about 350 mOsm/kg. pHs from about 4 to about 6 are preferred, with pHs from about 4.5 to 5.5 more preferred, such as, for example, about 4.5, about 4.6, about 4.7, about 4.8, about 4.9, about 5.0, about 5.1, about 5.2, about 5.3, about 5.4 and about 5.5.

The oral solutions of the present invention may optionally comprise other excipients. The solutions may contain, inter alia, acids, bases or buffer substances for adjusting the pH, e.g., citric acid, sodium citrate, phosphoric acid, sodium phosphate as well as mixtures of citrate and phosphate buffers; preservatives, e.g., sulfites (sulfur dioxide, sodium bisulfite, and potassium hydrogen sulfite), propionates (propionic acid, calcium propionate, and sodium propionate), benzoates (sodium benzoate, and benzoic acid), sorbates (potassium sorbate, sodium sorbate, calcium sorbate, and sorbic acid), nitrates (sodium nitrate), nitrites (sodium nitrite) and methyl paraben; high potency sweeteners, e.g. sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I; and flavoring agents, e.g. peppermint oil, spearmint oil, other mint oils, clove oil, cinnamon oil, oil of wintergreen, bay, thyme, cedar leaf, nutmeg, allspice, sage, mace, almonds, apple, banana, watermelon, pear, peach, grape, strawberry, raspberry, cherry, plum, pineapple, apricot, lemon, lime, orange, tangerine, grapefruit, citron, or kumquat. Natural or artificial flavoring agents can be used.

In one embodiment, the oral solution further comprises buffering substances in an amount from about 0.5% to about 1.5%, by weight such as, for example, about 0.5%, about 0.6%, about 0.7%, about 0.8%, about 0.9%, about 1.0%, about 1.1%, about 1.2%, about 1.3%, about 1.4% or about 1.5%. In a more particular embodiment, the buffering substances are sodium citrate and citric acid in an amount of about 0.9%.

In another embodiment, the oral solution further comprises at least one preservative in an amount from about 0.10% to about 0.50% by weight, such as, for example, about 0.10%, about 0.15%, about 0.20%, about 0.25%, about 0.30%, about 0.35%, about 0.40%, about 0.45% or about 0.50%.

In a more particular embodiment, the preservative is sodium benzoate in an amount of about 0.25%.

In still another embodiment, the oral solution further comprises at least one high potency sweetener from about 0.010% to about 0.050% by weight, such as, for example, about 0.010%, about 0.015%, about 0.020%, about 0.025%, about 0.030%, about 0.035%, about 0.040%, about 0.045% or about 0.050%. In a more particular embodiment, the high potency sweetener is sucralose in an amount of about 0.025%.

In yet another embodiment, the oral solution further comprises at least one flavor ingredient in an amount from about 0.10% to about 0.50% by weight, such as, for example, about 0.10%, about 0.15%, about 0.20%, about 0.25%, about 0.30%, about 0.35%, about 0.40%, about 0.45% or about 0.50%. In a more particular embodiment, the flavor ingredient is artificial grape flavor in an amount of about 0.25%.

In a particular embodiment, the oral solution comprises water in an amount of about 95% to about 99% by weight, sotalol hydrochloride in an amount from about 0.2% to about 8% by weight, at least one buffering substance, at least one preservative, and optionally, at least one high potency sweetener and at least one flavor ingredient.

In a particular embodiment, the oral solution comprises water in an amount of about 95% to about 99%, sotalol hydrochloride in an amount from about 0.2% to about 8%, buffering substances in an amount from about 0.5% to about 1.5%, at least one preservative in an amount from about 0.10% to about 0.50%, at least one high potency sweetener from about 0.010% to about 0.050% and at least one flavor ingredient in an amount from about 0.10% to about 0.50%. All percentages are given by weight.

In another particular embodiment, an oral solution comprises water in an amount of about 95% to about 99%, sotalol hydrochloride in an amount from about 0.2% to about 8%, sodium citrate and citric acid in an amount from about 0.5% to about 1.5%, sodium benzoate in an amount from about 0.10% to about 0.50%, sucralose in an amount from about 0.010% to about 0.050% and artificial grape flavor in an amount from about 0.10% to about 0.50%. All percentages are given my weight.

In yet another particular embodiment, the oral solution comprises water in an amount of about 98%, sotalol hydrochloride in an amount of about 0.5%, sodium citrate and citric acid in an amount of about 0.9%, sodium benzoate in an amount of about 0.25%, sucralose in an amount of about 0.025% and artificial grape flavor in an amount of about 0.25%. All percentages are given by weight.

III. Methods of Use

The present invention also provides for methods of treating a disease or disorder comprising administering the oral solutions of the present invention to a host in need thereof.

As used herein, "treatment" or "treat" means any treatment of a disease or disorder in a host such as a mammal, including: (a) protecting against the disease or disorder, that is, causing the clinical symptoms not to develop; (b) inhibiting the disease or disorder, that is, arresting, ameliorating, reducing, or suppressing the development of clinical symptoms; and/or (c) relieving the disease or disorder, that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The host may be, for example, any living mammal in need or likely in need of treatment, including primates, in particular humans, and other mammals such as, for example, equines, cattle, swine, sheep, felines, canines, poultry and domestic pets in general. In a particular embodiment, the patient is a human, more particularly a human unable to swallow tablets, e.g. children and/or the elderly.

Such methods of treatment would have particular utility in numerous therapeutic settings (as well as others which may be determined by someone skilled in the art) including, but not limited to treatment of diseases or disorders of the heart, including but not limited:
  i) Acute control and prevention of the recurrences of life-threatening disorders of rhythm such as ventricular tachycardia and ventricular fibrillation occurring in patients with coronary artery disease;
  ii) Prevention of defibrillator shocks in patients with implantable devices for the prevention of sudden death;
  iii) Termination and prevention of recurrences of atrial fibrillation and flutter in patients;
  iv) Prevention of the occurrences of atrial fibrillation by prophylactic administration;
  v) Symptomatic control of angina pectoris in patients still experiencing chest pain after cardiac surgery, after myocardial infarction, or patients with coronary artery disease not amenable to treatment by surgery or angioplasty;
  vi) Control of systemic systolic and diastolic high blood pressure;
  vii) Adjunctive therapy for the control of heart rate and atrial fibrillation in the initial acute stages of hyperthyroidism;
  viii) Control of atrial fibrillation, myocardial ischemia in the setting of ischemic heart disease, and hypertension simultaneously occurring;
  ix) Control of fetal tachycardias; and
  x) Other uses of sotalol hydrochloride that have therapeutic activity for any purpose.

In a particular embodiment, the present invention is a method for delaying recurrence of atrial fibrillation/atrial flutter comprising administering an oral solution of the present invention to a host in need thereof.

In another particular embodiment, the present invention is a method for treating documented life-threatening ventricular arrhythmias comprises administering an oral solution of the present invention to a host in need thereof.

The dosing protocol can be determined by a physician or other appropriate treatment supervisor in light of the relevant circumstances including, for example, age, weight, response of the individual patient, severity of the patient's symptoms and/or creatine clearance ability. Patients should of course be monitored for possible adverse events.

In one embodiment, the dose of the oral solution administered is bioequivalent to about sotalol hydrochloride in pill form. In a preferred embodiment, dosing of an oral solution of the present invention is consistent with dosing for commercially available Betapace.

In one embodiment, the host is administered a 80 mg daily dose, a 100 mg daily dose, a 120 mg daily dose, a 140 mg daily dose, a 160 mg daily dose, a 180 mg daily dose, a 200 mg daily dose, a 220 mg daily dose, a 240 mg daily dose, a 260 mg daily dose, a 280 mg daily dose, a 300 mg daily dose, a 320 mg daily dose, a 340 mg daily dose or a 360 mg daily dose of the oral solution.

Administration of the oral solution may occur once, twice or three times a day.

In one embodiment, the host is administered an 80 mg daily dose of the oral solution, once a day.

In another embodiment, the host is administered an 80 mg daily dose of the oral solution, once a day.

In one embodiment, the method comprises administering the oral solution to a host in need thereof in an initial oral dose of about 80 mg, once or twice daily, based on creatine clearance.

In a particular embodiment, the oral solution is administered in an initial dose of about 80 mg twice a day to a host in need thereof with a creatine clearance greater than 60 mL/min.

In another particular embodiment, the oral solution is administered in an initial dose of about 80 mg once a day in a host in need thereof with a creatine clearance between 40 and 60 mL/min.

In exemplary embodiments, the dose is increased up to 320 mg once or twice a day, depending on creatine clearance, if the 80 mg dose does not effectively provide treatment for the host to which it was administered (e.g., the 80 mg treatment does not reduce frequency of life-threatening disorders of rhythm such as ventricular tachycardia or reduce symptomatic atrial fibrillation and flutter).

In a particular embodiment, the dose may be increased in increments of 80 mg per day for three days. QTc should be monitored during dose escalation.

In some embodiments, the oral solution is administered in a dose up to 160 mg one or twice a day to a host in need thereof.

In other embodiments, the oral solution is administered in a dose up to 240 mg one or twice a day to a host in need thereof.

In still further embodiments, the oral solution is administered in a dose up to 320 mg once or twice a day to a host in need thereof.

In one embodiment, the host in need thereof is a child aged about 2 years or older, with normal renal function, and the dose administered is normalized for body surface area for both initial and incremental dosing. Since the Class III potency in children is not very different from that in adults, reaching plasma concentrations that occur within the adult dose range is an appropriate guide. In a particular embodiment, the oral solution is administered in an initial dose of about 30 mg/m$^2$ three times a day (90 mg/m$^2$ total daily dose). This dose is approximately equivalent to an initial 160 mg total daily dose for adults. Subsequent titration to a maximum of 60 mg/m$^2$ (approximately equivalent to the 360 mg total daily dose for adults) can then occur. Titration should be guided by clinical response, heart rate and QTc, with increased dosing being preferably carried out in-hospital. At least 36 hours should be allowed between dose increments to attain steady-state plasma concentrations of sotalol in patients with age-adjusted normal renal function.

For children aged about 2 years or younger, the above pediatric dosage may be reduced by a factor that depends heavily upon age.

In one embodiment, the dose for a child aged 20 months is the dose suggested for children with normal renal function aged 2 years or greater multiplied by about 0.97; the initial starting dose would be (30×0.97)=29.1 mg/m$^2$, administered three times daily.

In another embodiment, the dose for a child aged 1 month, the starting dose should be multiplied by 0.68; the initial starting dose would be (30×0.68)=20 mg/m$^2$, administered three times daily.

For a child aged about 1 week, the initial starting dose should be multiplied by 0.3; the starting dose would be (30×0.3)=9 mg/m$^2$. Similar calculations should be made for increased doses as titration proceeds.

The oral solution may be administered before, together with, or after intake of food.

IV. Methods of Preparation

The present invention also extends to methods of preparing or manufacturing the oral solutions of the present invention.

In one embodiment, the method of preparation comprises admixing by admixing sotalol hydrochloride with water.

In a particular embodiment, the method of preparation comprises admixing sotalol hydrochloride and one or more excipients with water.

The oral solution of the present invention is prepared by completely dissolving the sotalol hydrochloride and optionally the excipients, in solution.

An exemplary embodiment of the method of preparation is provided in Example 1, hereto.

EXAMPLES

Example 1: Oral Sotalol Solution and Preparation of the Same

| Material | % w/w |
|---|---|
| Purified Water | 98.075 |
| Citric Acid Monohydrate | 0.260 |
| Sodium Citrate Dihydrate | 0.640 |
| Sucralose | 0.025 |
| Sodium Benzoate | 0.250 |
| Sotalol HCl | 0.500 |
| Artificial Grape Flavor | 0.250 |

Manufacturing Process for Sotalol Hydrochloride Oral Solution (5 mg/mL)

Purified Water to the amount of 75% of the formulation (525 kg) was added to a 2300 L stainless steel mixing tank equipped with a variable speed mixer. The mixer was set at a speed to maintain a vortex. The raw materials were added to the batch in the order listed in the table above. Each material was added separately and mixed until dissolved. The temperature and mixing time for each addition was recorded. Once all of the raw materials were added, the batch was brought to a final target weight of 700 kg with purified water and mixed. The batch was then passed through an in-line filter housing equipped with a 10 μm cartridge filter into a holding tank. The specific gravity, pH, and final batch yield of each batch was determined. A summary of the manufacturing process and process parameters is outlined below:

| Summary of Manufacturing Steps and Process Parameters for the Manufacture of Sotalol Hydrochloride Oral Solution 5 mg/mL | | | |
|---|---|---|---|
| Manufacturing Step | MFYN | MFYP | MFYS |
| Charge Purified Water to 2300 L Mixing Tank. record temperature (° C.) | 22.9 | 22.9 | 22.2 |
| Set variable speed mixer to maintain vortex (rpm) | 280 | 285 | 280 |
| Charge Citric Acid Monohydrate and mix until dissolved, | | | |
| Mixing Time (min) | 10 | 10 | 10 |
| Temperature (° C.) | 21.2 | 22.4 | 20.6 |
| Charge Sodium Citrate Dihydrate and mix until dissolved | | | |
| Mixing Time (min) | 10 | 10 | 10 |
| Temperature (° C.) | 20.5 | 22.2 | 20.5 |
| Charge Sucralose and mix until dissolved, | | | |
| Mixing Time (nun) | 10 | 10 | 10 |
| Temperature (° C.) | 17.7 | 22.6 | 16.6 |
| Charge Sodium Benzoate and mix until dissolved, | | | |
| Mixing Time (min) | 10 | 10 | 10 |
| Temperature (° C.) | 20.5 | 22.4 | 19.8 |
| Charge Sotalol Hydrochloride USP and mix until dissolved, | | | |
| Mixing Time (min) | 10 | 10 | 10 |
| Temperature (° C.) | 21.0 | 22.1 | 20.9 |
| Charge Grape Flavor and mix until dissolved, | | | |
| Mixing Time (min) | 10 | 10 | 10 |
| Temperature (° C.) | 21.3 | 22.1 | 21.2 |
| Determine Net Wt. Of solution (kg) | 539.0 | 534.0 | 536.5 |
| Adjust the batch weight to target of 700.0 kg with Purified Water | | | |
| Amount of Purified Water to q.s. | 161.0 | 166.0 | 163.5 |
| Mix for additional 10 minutes | | | |
| Mixing Time (min) | 10 | 10 | 10 |
| Temperature (° C.) | 21.4 | 22.3 | 20.6 |
| Mixing Speed (rpm) | 280 | 285 | 280 |
| Determine Specific Gravity of Solution | 1.008 | 1.008 | 1.010 |
| Determine pH of Solution | | | |
| pH | 5.00 | 4.98 | 5.04 |
| Temperature (° C.) | 24.2 | 24.4 | 23.6 |
| Using the pump, transfer solution to holding tank through in-line filter housing with 10 μm cartridge filter | | | |
| Final Batch Weight after transfer (kg) | 696.6 | 698.4 | 697.2 |
| Convert batch size to liters (L) | 691.1 | 692.9 | 690.3 |
| Sample Weight (kg) | 0.7 | 0.7 | 0.7 |

Example 2: Preparation of Sotalol Extemporaneous Suspension

The extemporaneous suspension was prepared according to the labeling for the commercially available sotalol hydrochloride tablets, i.e. 5 tablets (120 mg each) were added to 120 mL of Simple Syrup with 0.1% sodium benzoate (Syrup N.F.) in an oversized (180 mL) plastic (PET) prescription bottle. The tablets were allowed to hydrate for at least 2 hours, then shaken intermittently over the course of at least another 2 hours until the tablets were completely disintegrated. A dispersion of fine particles was obtained. The tablets were then allowed to hydrate overnight to simplify disintegration process. The resulting preparation contains 5 mg/mL of sotalol hydrochloride in solution with suspended inactive solid particles (water-insoluble tablet ingredients).

Example 3: pH and Osmolality of Standard Preparations

The pH and osmolality for the solution in Example 1 and the suspension in Example 2 were determined:

| Undiluted Sample | pH | Osmolality (mOsm/kg) |
|---|---|---|
| Sotalol HCl Oral Solution (Example 1) | 5.1 | 212 |
| Sotalol HCl Tablets in H$_2$O | 5.4 | 39 |
| Sotalol Extemporaneous Suspension (Example 2) | 2.4 | 2680 |

The results showed that the osmolality for the sotalol HCl solution (Example 1) falls within range of the osmolality for the marketed Sotalol HCl tablet and the osmolality of the extemporaneously prepared suspension. Likewise, the pH for the sotalol HCl solution falls within range of the pH for the marketed Sotalol HCl tablet and the pH of the extemporaneously prepared suspension. Notable differences were found in pH and osmolality between the oral solution and the extemporaneous suspension.

Example 4: pH and Osmolality of Diluted Preparations

Dilutions of 80 mg (16 mL) doses of the Sotalol HCl solutions/suspensions were made with diluents of different pH. The pH and Osmolality results for the diluted Sotalol preparations are shown in the table below.

| Sotalol HCl tablets | pH | Osmolality | Sotalol HCl Solution | pH | Osmolality | Sotalol Extemporaneous Suspension | pH | Osmolality |
|---|---|---|---|---|---|---|---|---|
| A | 4.5 | 291 | A | 4.5 | 318 | A | 4.5 | 843 |
| B | 7.0 | 94 | B | 6.7 | 118 | B | 6.9 | 603 |
| C | 1.7 | 73 | C | 1.9 | 84 | C | 1.5 | 601 |
| D | 5.6 | 4 | D | 5.6 | 26 | D | 4.1 | 517 |

A: For tablets: Sotalol HCl tablets in DI water, diluted with pH 4.5 acetate buffer;
For Sotalol HCl solution and suspension: diluted with pH 4.5 acetate buffer
B: For tablets: Sotalol HCl tablets in DI water, diluted with pH 6.8 phosphate buffer;
For Sotalol HCl solution and suspension: diluted with pH 6.8 phosphate buffer
C: For tablets: Sotalol HCl tablets in DI water, diluted with pH~1 HCl;
For Sotalol HCl solution and suspension: diluted with pH~1 HCl
D: For tablets: Sotalol HCl tablets in DI water, diluted with DI water;
For Sotalol HCl solution and suspension: diluted with DI water The results of this assessment showed that the osmolality for the sotalol HCl solution in different pH dilutions falls within range of the osmolality values for the marketed Sotalol HCl tablet and the osmolality values of the extemporaneously prepared suspension.

Example 5: Stability Studies of Sotalol Hydrochloride Oral Solution (5 mg/mL)

Stability data up to 11 months at 25° C./60% relative humidity (RH) and 30° C./65% RH and up to 6 months at 40° C./75% RH for three registration batches of Sotalol Hydrochloride Oral Solution (batches MFYN, MFYP, and MFYS), representing the commercial process and manufactured at the intended commercial supplier.

The three batches were packed in 250 mL and 480 mL bottles, representing six packaging batches. Sotalol Hydrochloride Oral Solution was packaged as a 250 mL product in a 250 mL, round, amber PET bottle with a 24 mm white HDPE child resistant cap with an induction seal. The product was also packaged as a 480 mL product in a 500 mL, round, amber, PET bottle with a 28 mm white HDPE child resistant cap with an induction seal. Photostability testing was performed on batch MFYN (packaged batches MHBV and MHBP) in compliance with International Conference on Harmonization (ICH) recommended storage conditions. Batches were stored in accordance with the following ICH conditions. The bottles were stored in the inverted and upright position.

| Drug Product Stability Storage Conditions | |
|---|---|
| Storage Condition | Description |
| 25° C./60% RH | 25° C. ± 2° C./60% ± 5% Relative Humidity (RH) |
| 40° C./75% RH | 40° C. ± 2° C./75% ± 5% Relative Humidity (RH) |
| 30° C./65% RH | 30° C. ± 2° C./76% ± 5% Relative Humidity (RH) |
| Photostability | ICH Q1B, Option 2 |

Stability Protocol for Sotalol Hydrochloride Oral Solution in 250 mL and 480 mL Bottles

| | | | Time point (months) | | | | | | | | | |
|---|---|---|---|---|---|---|---|---|---|---|---|---|
| | | | $0^a$ | $1^b$ | 3 | $6^d$ | $8^{e,d}$ | $9^d$ | $11^{c,d}$ | $12^{d,e}$ | 18 | $24^c$ | $36^e$ |
| Packaging Configuration | 250 mL (upright) | MHBS | T | T | T | T | T | T | T | T | | T | T |
| | | MHBT | T | T | T | T | T | T | T | T | T | | T |
| | | MHBP | T | T | T | T | T | | T | T | T | | T |
| | 480 mL (upright) | MHBW | T | T | T | T | T | | T | T | | T | T |
| | | MHBX | T | T | T | T | T | T | T | T | T | | T |
| | | MHBV | T | T | T | T | T | | T | T | | T | T |
| Packaging Configuration | 250 mL (inverted) | MHBS | T | T | T | T | T | | T | T | T | | T |
| | | MHBT | T | T | T | T | T | | T | T | | T | T |
| | | MHBP | T | T | T | T | T | T | T | T | | T | T |
| | 480 mL (inverted) | MHBW | T | T | T | T | T | T | T | T | T | | T |
| | | MHBX | T | T | T | T | T | | T | T | | T | T |
| | | MHBV | T | T | T | T | T | T | T | T | T | | T |

Key:
T = Samples will be tested at all temperatures unless noted otherwise (appearance, appearance of packaging, pH, osmolality, sodium benzoate assay, sotalol HCl assay, related substances)
$^a$ID and specific gravity only tested at T = 0
$^b$40° C./75% RH testing only
$^c$includes micro and AET testing
$^d$includes 30° C./65% RH testing
$^e$includes micro testing
Water loss is only conducted at 25° C./60% RH The results of these studies are shown in the tables that follow. The abbreviations have the following meanings:
NR=Not required  TAMC=Total aerobic microbial count
ND=Not detected  TYCM=Total combined yeasts and molds count

TABLE 1

Stability of 250 mL at 25° C./60% RH

| | | | 3 month | | 6 month | | 8 month | | 9 month$^a$ | 11 month | |
|---|---|---|---|---|---|---|---|---|---|---|---|
| | | Initial | Upright | Inverted | Upright | Inverted | Upright | Inverted | Inverted | Upright | Inverted |
| Date Samples Pulled | | Apr. 4, 2013 | Jul. 9, 2013 | Jul. 9, 2013 | Oct. 4, 2013 | Oct. 4, 2013 | Dec. 2, 2013 | Dec. 2, 2013 | Jan. 9, 2014 | Feb. 28, 2014 | Feb. 28, 2014 |
| Appearance | Clear, colorless liquid | Complies | Complies | Complies | Complies | Complies | Complies | Complies | Complies | Complies | Complies |
| Appearance of Packaging | 250 mL, amber PET round bottle; white child resistant cap with induction seal. No visible damage to any of the components | Complies | Complies | Complies | Complies | Complies | Complies | Complies | Complies | Complies | Complies |
| Identification of Sotalol HCl by HPLC | Exhibits major peak for Sotalol; Retention time is the same as that of reference standard | Complies | NR | NR | NR | NR | NR | NR | NR | NR | NR |
| Identification of Sotalol HCl by UV | The spectrum of the main peak in the sample chromatogram matches the spectrum of the main peak in the standard chromatogram | Complies | NR | NR | NR | NR | NR | NR | NR | NR | NR |

TABLE 1-continued

Stability of 250 mL at 25° C./60% RH

| | | Initial | 3 month Upright | 3 month Inverted | 6 month Upright | 6 month Inverted | 8 month Upright | 8 month Inverted | 9 month[a] Inverted | 11 month Upright | 11 month Inverted |
|---|---|---|---|---|---|---|---|---|---|---|---|
| Assay for Sotalol HCl | 90.0%-110.0% of theoretical | 1) 101.9% 2) 101.6% Mean: 101.8% | 1) 99.7% 2) 99.7% Mean: 99.7% | 1) 99.7% 2) 99.8% Mean: 99.8% | 1) 101.3% 2) 101.5% Mean: 101.4% | 1) 101.7% 2) 101.9% Mean: 101.8% | 1) 101.0% 2) 102.6% Mean: 101.8% | 1) 102.6% 2) 101.4% Mean: 102.0% | 1) 101.3% 2) 101.7% Mean: 101.5% | 1) 102.3% 2) 102.3% Mean: 102.3% | 1) 101.7% 2) 102.0% Mean: 101.9% |
| Related Substances | Related Compound A: NMT 0.2% | ND | ND | ND | ND | ND | ND | ND | ND | ND | ND |
| | Related Compound B: NMT 0.2% | ND | ND | ND | ND | ND | ND | ND | ND | ND | ND |
| | Related Compound C: NMT 0.2% | ND | ND | ND | ND | ND | ND | ND | ND | ND | ND |
| | Unknown Impurities: NMT 0.1% | RRT 0.74: 0.10% RRT 2.12: 0.05% | ND | ND | <QL | <QL | RRT 2.16: <QL RRT 2.75: 0.05 RRT 3.67: <QL | RRT 2.17: <QL RRT 2.77: 0.05 RRT 3.70: <QL | RRT 2.10: 0.05 RRT 2.61: 0.06 | RRT 2.12: <QL RRT 2.84: 0.09% | RRT 2.12: <QL RRT 2.83: 0.09% |
| | Total Impurities: NMT 2.5% | 0.15% | ND | ND | <QL | <QL | 0.05% | 0.05% | 0.11% | 0.09% | 0.09% |
| Assay of Sodium Benzoate | 80.0%-110.0% of theoretical | 1) 100.4% 2) 100.5% Mean: 100.5% | 1) 101.2% 2) 101.9% Mean: 101.6% | 1) 102.5% 2) 102.4% Mean: 102.5% | 1) 102.1% 2) 102.5% Mean: 102.3% | 1) 101.0% 2) 101.8% Mean: 101.4% | 1) 101.1% 2) 100.6% Mean: 100.9% | 1) 101.1% 2) 101.1% Mean: 101.1% | 1) 101.0% 2) 100.8% Mean: 100.9% | 1) 100.6% 2) 100.8% Mean: 100.7% | 1) 100.7% 2) 100.9% Mean: 100.8% |
| pH | 4.5-5.5 | 5.05 | 5.0 | 5.0 | 5.0 | 5.0 | 5.0 | 5.0 | 5.0 | 5.0 | 5.0 |
| Osmolality | ≤400 | 182 mOsm/kg | 181 mOsm/kg | 183 mOsm/kg | 184 mOsm/kg | 184 mOsm/kg | 182 mOsm/kg | 183 mOsm/kg | 184 mOsm/kg | 187 mOsm/kg | 187 mOsm/kg |
| Specific Gravity | Report result | 1.0077 | NR | NR | NR | NR | NR | NR | NR | NR | NR |
| Microbial Limits | TAMC: NMT $10^2$ cfu/mL | <10 cfu/mL | NR | NR | NR | NR | <10 cfu/mL | <10 cfu/mL | NR | <10 cfu/mL | <10 cfu/mL |
| | TCYM: NMT $10^1$ cfu/mL | <10 cfu/mL | | | | | <10 cfu/mL | <10 cfu/mL | | <10 cfu/mL | <10 cfu/mL |
| | E. Coli: Absent/mL | Absent/mL | | | | | Absent/mL | Absent/mL | | Absent/mL | Absent/mL |
| | S. aureus: Absent/mL | Absent/mL | | | | | Absent/mL | Absent/mL | | Absent/mL | Absent/mL |
| | P. aeruginosa: Absent/mL | Absent/mL | | | | | Absent/mL | Absent/mL | | Absent/mL | Absent/mL |
| | Salmonella: Absent/10 mL | Absent/10 mL | | | | | Absent/10 mL | Absent/10 mL | | Absent/10 mL | Absent/10 mL |
| | B. cepacia: Absent/mL | Absent/mL | | | | | Absent/mL | Absent/mL | | Absent/mL | Absent/mL |
| AET | Meets acceptance criteria stated in USP<51> | Pass | NR | NR | NR | NR | Pass | Pass | NR | Pending | Pending |
| Water Loss | Report result | NR | Mean: 0.2735% | Mean: 0.2739% | Mean: 0.5595% | Mean: 0.5781% | Mean: 0.7467% | Mean: 0.7444% | Mean: 0.8719% | Mean: 1.0290% | Mean: 1.0335% |

[a] Alternate orientation not required due to stability matrixing

TABLE 2

Stability of 480 mL at 25° C./60% RH

| | | Initial | 3 month Upright | 3 month Inverted | 6 month Upright | 6 month Inverted | 8 month Upright | 8 month Inverted | 9 month[a] Inverted | 11 month Upright | 11 month Inverted |
|---|---|---|---|---|---|---|---|---|---|---|---|
| Date Samples Pulled | | Apr. 4, 2013 | Jul. 9, 2013 | Jul. 9, 2013 | Oct. 4, 2013 | Oct. 4, 2013 | Dec. 2, 2013 | Dec. 2, 2013 | Jan. 9, 2014 | Feb. 28, 2014 | Feb. 28, 2014 |
| Appearance | Clear, colorless liquid | Complies | Complies | Complies | Complies | Complies | Complies | Complies | Complies | Complies | Complies |
| Appearance of Packaging | 480 mL, amber PET round bottle; | Complies | Complies | Complies | Complies | Complies | Complies | Complies | Complies | Complies | Complies |

TABLE 2-continued

Stability of 480 mL at 25° C./60% RH

| | | Initial | 3 month Upright | 3 month Inverted | 6 month Upright | 6 month Inverted | 8 month Upright | 8 month Inverted | 9 month[a] Inverted | 11 month Upright | 11 month Inverted |
|---|---|---|---|---|---|---|---|---|---|---|---|
| | white child resistant cap with induction seal. No visible damage to any of the components | | | | | | | | | | |
| Identification of Sotalol HCl by HPLC | Exhibits major peak for Sotalol; Retention time is the same as that of reference standard | Complies | NR | NR | NR | NR | NR | NR | NR | NR | NR |
| Identification of Sotalol HCl by UV | The spectrum of the main peak in the sample chromatogram matches the spectrum of the main peak in the standard chromatogram | Complies | NR | NR | NR | NR | NR | NR | NR | NR | NR |
| Assay for Sotalol HCl | 90.0%-110.0% of theoretical | 1) 101.0% 2) 102.1% Mean: 101.6% | 1) 101.3% 2) 101.5% Mean: 101.4% | 1) 101.0% 2) 101.4% Mean: 101.2% | 1) 102.4% 2) 102.5% Mean: 102.5% | 1) 102.3% 2) 102.2% Mean: 102.3% | 1) 102.3% 2) 103.3% Mean: 102.8% | 1) 102.4% 2) 103.8% Mean: 103.1% | 1) 101.6% 2) 100.9% Mean: 101.3% | 1) 102.0% 2) 102.1% Mean: 102.1% | 1) 101.7% 2) 101.9% Mean: 101.8% |
| Related Substances | Related Compound A: NMT 0.2% | ND | ND | ND | ND | ND | ND | ND | ND | ND | ND |
| | Related Compound B: NMT 0.2% | ND | ND | ND | ND | ND | ND | ND | ND | <QL | <QL |
| | Related Compound C: NMT 0.2% | ND | ND | ND | ND | ND | ND | ND | ND | ND | ND |
| | Unknown Impurities: NMT 0.1% | RRT 0.74: 0.14% RRT 2.12: <QL | RRT 0.78: <QL RRT 2.04: <QL | RRT 0.78: 0.05% RRT 2.04: <QL | <QL | <QL | RRT 2.16: <QL RRT 2.75: <QL | RRT 2.22: <QL RRT 2.82: <QL RRT 3.45: <QL | RRT 2.09: <QL RRT 2.60: 0.06% | RRT 2.13: 0.06% RRT 2.63: <QL RRT 2.92: 0.08% | RRT 2.14: 0.06% RRT 2.91: 0.08% |
| | Total Impurities: NMT 2.5% | 0.14% | <QL | 0.05% | <QL | <QL | <QL | <QL | 0.06% | 0.09% | 0.14% |
| Assay of Sodium Benzoate | 80.0%-110.0% of theoretical | 1) 100.0% 2) 99.9% Mean: 100.0% | 1) 101.7% 2) 102.4% Mean: 102.1% | 1) 101.5% 2) 101.4% Mean: 101.5% | 1) 101.5% 2) 102.1% Mean: 101.8% | 1) 102.6% 2) 102.0% Mean: 102.3% | 1) 101.0% 2) 100.9% Mean: 101.0% | 1) 100.9% 2) 101.1% Mean: 101.0% | 1) 101.1% 2) 101.7% Mean: 101.4% | 1) 100.4% 2) 100.3% Mean: 100.4% | 1) 100.6% 2) 100.5% Mean: 100.6% |
| pH | 4.5-5.5 | 5.06 | 5.0 | 5.0 | 5.0 | 5.0 | 5.0 | 5.0 | 5.0 | 5.0 | 5.0 |
| Osmolality | ≤400 mOsm/kg | 182 mOsm/kg | 183 mOsm/kg | 182 mOsm/kg | 182 mOsm/kg | 184 mOsm/kg | 183 mOsm/kg | 183 mOsm/kg | 183 mOsm/kg | 187 mOsm/kg | 185 mOsm/kg |
| Specific Gravity | Report result | 1.0076 | NR | NR | NR | NR | NR | NR | NR | NR | NR |
| Microbial Limits | TAMC: NMT $10^2$ cfu/mL | <10 cfu/mL | NR | NR | NR | NR | <10 cfu/mL | <10 cfu/mL | NR | <10 cfu/mL | <10 cfu/mL |
| | TCYM: NMT $10^1$ cfu/mL | <10 cfu/mL | | | | | <10 cfu/mL | <10 cfu/mL | | <10 cfu/mL | <10 cfu/mL |
| | *E. Coli*: Absent/Absent/mL | Absent/mL | | | | | Absent/mL | Absent/mL | | Absent/mL | Absent/mL |
| | *S. aureus*: Absent/Absent/mL | Absent/mL | | | | | Absent/mL | Absent/mL | | Absent/mL | Absent/mL |
| | *P. aeruginosa*: Absent/Absent/mL | Absent/mL | | | | | Absent/mL | Absent/mL | | Absent/mL | Absent/mL |
| | *Salmonella*: Absent/Absent/10 mL | Absent/10 mL | | | | | Absent/10 mL | Absent/10 mL | | Absent/10 mL | Absent/10 mL |
| | *B. cepacia*: Absent/Absent/mL | Absent/mL | | | | | Absent/mL | Absent/mL | | Absent/mL | Absent/mL |

TABLE 2-continued

| | | | 3 month | | 6 month | | 8 month | | 9 month[a] | 11 month | |
|---|---|---|---|---|---|---|---|---|---|---|---|
| | | Initial | Upright | Inverted | Upright | Inverted | Upright | Inverted | Inverted | Upright | Inverted |
| AET | Meets acceptance criteria stated in USP<51> | Pass | NR | NR | NR | NR | Pass | Pass | NR | Pending | Pending |
| Water Loss | Report result | NR | Mean: 0.2875% | Mean: 0.3813%* | Mean: 0.5618% | Mean: 0.7028%* | Mean: 0.7311% | Mean: 0.9449%* | Mean: 1.0987%* | Mean: 1.0167% | Mean: 1.2630%* |

[a] Alternate orientation not required due to stability matrixing
*OOS64084 for an individual water loss due to leaking bottle #1

TABLE 3

Stability of 250 mL at 30° C./60% RH

| | | Initial | 6 month | | 8 month | | 9 month | | 11 month | |
|---|---|---|---|---|---|---|---|---|---|---|
| | | | Upright | Inverted | Upright | Inverted | Upright | Inverted | Upright | Inverted |
| Date Samples Pulled | | Apr. 4, 2013 | Oct. 4, 2013 | Oct. 4, 2013 | Dec. 2, 2013 | Feb. 28, 2014 | Jan. 9, 2014 | Jan. 9, 2014 | Feb. 28, 2014 | Feb. 28, 2014 |
| Appearance | Clear, colorless liquid | Complies | Complies | Complies | Complies | Complies | Complies | Complies | Complies | Complies |
| Appearance of Packaging | 250 mL, amber PET round bottle; white child resistant cap with induction seal. No visible damage to any of the components | Complies | Complies | Complies | Complies | Complies | Complies | Complies | Complies | Complies |
| Identification of Sotalol HCl by HPLC | Exhibits major peak for Sotalol; Retention time is the same as that of reference standard | Complies | NR | NR | NR | NR | NR | NR | NR | NR |
| Identification of Sotalol HCl by UV | The spectrum of the main peak in the sample chromatogram matches the spectrum of the main peak in the standard chromatogram | Complies | NR | NR | NR | NR | NR | NR | NR | NR |
| Assay for Sotalol HCl | 90.0%-110.0% of theoretical | 1) 101.9% 2) 101.6% Mean: 101.8% | 1) 100.5% 2) 100.4% Mean: 100.5% | 1) 100.6% 2) 100.3% Mean: 100.5% | 1) 101.0% 2) 101.5% Mean: 101.3% | 1) 101.8% 2) 102.1% Mean: 102.0% | 1) 101.5% 2) 101.6% Mean: 101.6% | 1) 100.6% 2) 101.6% Mean: 101.1% | 1) 101.8% 2) 102.1% Mean: 102.0% | 1) 101.8% 2) 101.9% Mean: 101.9% |
| Related Substances | Related Compound A: NMT 0.2% | ND | ND | ND | ND | ND | ND | ND | ND | ND |
| | Related Compound B: NMT 0.2% | ND | ND | ND | ND | ND | ND | ND | ND | ND |
| | Related Compound C: NMT 0.2% | ND | ND | ND | ND | ND | ND | ND | ND | ND |

TABLE 3-continued

Stability of 250 mL at 30° C./60% RH

| | | Initial | 6 month Upright | 6 month Inverted | 8 month Upright | 8 month Inverted | 9 month Upright | 9 month Inverted | 11 month Upright | 11 month Inverted |
|---|---|---|---|---|---|---|---|---|---|---|
| | Unknown Impurities: NMT 0.1% | RRT 0.74: 0.10% RRT 2.12: 0.05% | <QL | RRT 2.05: 0.06% RRT 2.10: 0.05% RRT 2.66: 0.10% | RRT 2.76: 0.11% RRT 3.69: <QL | RRT 2.12: <QL RRT 2.83: 0.17%* RRT 2.95: <QL | RRT 2.10: 0.05% RRT 2.62: 0.13% RRT 2.72: <QL | RRT 2.10: 0.05% RRT 2.61: 0.13% RRT 2.71: <QL | RRT 2.12: <QL RRT 2.83: 0.17% RRT 2.95: <QL | RRT 2.12: <QL RRT 2.84: 0.17% RRT 2.96: <QL |
| | Total Impurities: NMT 2.5% | 0.15% | <QL | 0.21% | 0.11% | 0.17% | 0.18% | 0.18% | 0.17% | 0.17% |
| Assay of Sodium Benzoate | 80.0%-110.0% of theoretical | 1) 100.4% 2) 100.5% Mean: 100.5% | 1) 101.8% 2) 102.4% Mean: 102.1% | 1) 102.1% 2) 102.3% Mean: 102.2% | 1) 101.4% 2) 101.1% Mean: 101.3% | 1) 101.1% 2) 101.0% Mean: 101.1% | 1) 101.4% 2) 100.2% Mean: 100.8% | 1) 101.2% 2) 101.7% Mean: 101.5% | 1) 101.1% 2) 101.0% Mean: 101.1% | 1) 100.9% 2) 101.1% Mean: 101.0% |
| pH | 4.5-5.5 | 5.05 | 5.0 | 5.0 | 5.0 | 5.0 | 5.0 | 5.0 | 5.0 | 5.0 |
| Osmolality | ≤400 mOsm/kg | 182 mOsm/kg | 186 mOsm/kg | 185 mOsm/kg | 182 mOsm/kg | 186 mOsm/kg | 184 mOsm/kg | 183 mOsm/kg | 186 mOsm/kg | 187 mOsm/kg |
| Specific Gravity | Report result | 1.0077 | NR | NR | NR | NR | NR | NR | NR | NR |
| Microbial Limits | TAMC: NMT $10^2$ cfu/mL TCYM: NMT $10^1$ cfu/mL E. Coli: Absent/mL S. aureus: Absent/mL P. aeruginosa: Absent/mL Salmonella: Absent/10 mL B. cepacia: Absent/mL | <10 cfu/mL <10 cfu/mL Absent/mL Absent/mL Absent/mL Absent/10 mL Absent/mL | NR | NR | NR | NR | NR | NR | NR | NR |
| AET | Meets acceptance criteria stated in USP<51> | Pass | NR | NR | NR | NR | NR | NR | NR | NR |
| Water Loss | Report result | NR | NR | NR | NR | NR | NR | NR | NR | NR |

*OOS66773

TABLE 4

Stability of 480 mL at 30° C./60% RH

| | | Initial | 6 month Upright | 6 month Inverted | 8 month Upright | 8 month Inverted | 9 month Upright | 9 month Inverted | 11 month Upright | 11 month Inverted |
|---|---|---|---|---|---|---|---|---|---|---|
| Date Samples Pulled | | Apr. 4, 2013 | Oct. 4, 2013 | Oct. 4, 2013 | Dec. 2, 2013 | Dec. 2, 2013 | Jan. 9, 2014 | Jan. 9, 2014 | Feb. 28, 2014 | Feb. 28, 2014 |
| Appearance | Clear, colorless liquid | Complies | Complies | Complies | Complies | Complies | Complies | Complies | Complies | Complies |
| Appearance of Packaging | 480 mL, amber PET round bottle; white child resistant cap with induction seal. No visible damage to any of the components | Complies | Complies | Complies | Complies | Complies | Complies | Complies | Complies | Complies |
| Identification of Sotalol HCl by HPLC | Exhibits major peak for Sotalol; Retention time is the | Complies | NR | NR | NR | NR | NR | NR | NR | NR |

TABLE 4-continued

Stability of 480 mL at 30° C./60% RH

|  |  |  | 6 month | | 8 month | | 9 month | | 11 month | |
| --- | --- | --- | --- | --- | --- | --- | --- | --- | --- | --- |
|  |  | Initial | Upright | Inverted | Upright | Inverted | Upright | Inverted | Upright | Inverted |
| Identification of Sotalol HCl by UV | same as that of reference standard The spectrum of the main peak in the sample chromatogram matches the spectrum of the main peak in the standard chromatogram | Complies | NR | NR | NR | NR | NR | NR | NR | NR |
| Assay for Sotalol HCl | 90.0%-110.0% of theoretical | 1) 101.0% 2) 102.1% Mean: 101.6% | 1) 100.7% 2) 100.8% Mean: 100.8% | 1) 100.5% 2) 100.7% Mean: 100.6% | 1) 101.8% 2) 102.3% Mean: 102.1% | 1) 102.5% 2) 103.5% Mean: 103.0% | 1) 100.6% 2) 101.0% Mean: 100.8% | 1) 101.5% 2) 100.7% Mean: 101.1% | 1) 102.4% 2) 102.7% Mean: 102.6% | 1) 102.0% 2) 102.3% Mean: 102.2% |
| Related Substances | Related Compound A: NMT 0.2% | ND | ND | ND | ND | ND | ND | ND | ND | ND |
|  | Related Compound B: NMT 0.2% | ND | ND | ND | ND | ND | ND | ND | <QL | <QL |
|  | Related Compound C: NMT 0.2% | ND | ND | ND | ND | ND | ND | ND | ND | ND |
|  | Unknown Impurities NMT 0.1% | RRT 0.74: 0.14% RRT 2.12: <QL | RRT 2.05: 0.05% RRT 2.10: 0.05% RRT 2.67: 0.11% | RRT 2.05: 0.06% RRT 2.10: 0.05% RRT 2.68: 0.10% RRT 2.79: <QL | RRT 2.17: <QL RRT 2.76: 0.11% | RRT 2.17: <QL RRT 2.75: 0.11% | RRT 2.10: <QL RRT 2.61: 0.13% RRT 2.71: <QL | RRT 2.60: 0.13% RRT 2.70: <QL | RRT 2.14: <QL RRT 2.62: <QL RRT 2.91: 0.17% RRT 3.04: <QL | RRT 2.13: 0.05% RRT 2.90: 0.17% RRT 3.02: <QL |
|  | Total Impurities: NMT 2.5% | 0.14% | 0.21% | 0.21% | 0.11% | 0.11% | 0.13% | 0.13% | 0.17% | 0.22% |
| Assay of Sodium Benzoate | 80.0%-110.0% of theoretical | 1) 100.0% 2) 99.9% Mean: 100.0% | 1) 102.4% 2) 102.9% Mean: 102.7% | 1) 102.2% 2) 102.3% Mean: 102.3% | 1) 101.3% 2) 101.4% Mean: 101.4% | 1) 101.3% 2) 101.1% Mean: 101.2% | 1) 100.3% 2) 101.6% Mean: 101.0% | 1) 102.1% 2) 101.6% Mean: 101.9% | 1) 100.4% 2) 100.5% Mean: 100.5% | 1) 100.8% 2) 101.3% Mean: 101.1% |
| pH | 4.5-5.5 | 5.06 | 5.0 | 5.0 | 5.0 | 5.0 | 5.0 | 5.0 | 5.0 | 5.0 |
| Osmolality | ≤400 | 182 mOsm/kg | 186 mOsm/kg | 184 mOsm/kg | 182 mOsm/kg | 183 mOsm/kg | 183 mOsm/kg | 185 mOsm/kg | 185 mOsm/kg | 185 mOsm/kg |
| Specific Gravity | Report result | 1.0076 | NR | NR | NR | NR | NR | NR | NR | NR |
| Microbial Limits | TAMC: NMT $10^2$ cfu/mL TCYM: NMT $10^1$ cfu/mL E. Coli: Absent/mL S. aureus: Absent/mL P. aeruginosa: Absent/mL Salmonella: Absent/10 mL B. cepacia: Absent/mL | <10 cfu/mL <10 cfu/mL Absent/ mL Absent/ mL Absent/ mL Absent/ 10 mL Absent/ mL | NR | NR | NR | NR | NR | NR | NR | NR |
| AET | Meets acceptance criteria stated in USP<51> | Pass | NR | NR | NR | NR | NR | NR | NR | NR |
| Water Loss | Report result | NR | NR | NR | NR | NR | NR | NR | NR | NR |

TABLE 5

Stability of 250 mL at 40° C./60% RH

| | | Initial | 1 month Upright | 1 month Inverted | 3 month Upright | 3 month Inverted | 6 month Upright | 6 month Inverted |
|---|---|---|---|---|---|---|---|---|
| Date Samples Pulled | | Apr. 4, 2013 | May 6, 2013 | May 6, 2013 | Jul. 9, 2013 | Jul. 9, 2013 | Oct. 4, 2013 | Oct. 4, 2013 |
| Appearance | Clear, colorless liquid | Complies | Complies | Complies | Complies | Complies | Complies | Complies |
| Appearance of Packaging | 250 mL, amber PET round bottle; white child resistant cap with induction seal. No visible damage to any of the components | Complies | Complies | Complies | Complies | Complies | Complies | Complies |
| Identification of Sotalol HCl by HPLC | Exhibits major peak for Sotalol; Retention time is the same as that of reference standard | Complies | NR | NR | NR | NR | NR | NR |
| Identification of Sotalol HCl by UV | The spectrum of the main peak in the sample chromatogram matches the spectrum of the main peak in the standard chromatogram | Complies | NR | NR | NR | NR | NR | NR |
| Assay for Sotalol HCl | 90.0%-110.0% of theoretical | 1) 101.5% 2) 101.4% Mean: 101.5% | 1) 100.4% 2) 100.8% Mean: 100.6% | 1) 100.7% 2) 100.6% Mean: 100.7% | 1) 100.3% 2) 99.9% Mean: 100.1% | 1) 99.5% 2) 100.0% Mean: 99.8% | 1) 102.2% 2) 102.0% Mean: 102.1% | 1) 101.7% 2) 101.3% Mean: 101.5% |
| Related Substances | Related Compound A: NMT 0.2% | ND | ND | ND | ND | ND | ND | ND |
| | Related Compound B: NMT 0.2% | ND | ND | ND | ND | ND | ND | ND |
| | Related Compound C: NMT 0.2% | ND | ND | ND | ND | ND | ND | ND |
| | Unknown Impurities: NMT 0.1% | RRT 0.74: 0.10% RRT 2.12: 0.05% | ND | ND | RRT 2.60: 0.15%* | RRT 2.62: 0.15%* | RRT 2.62: 0.25%* | RRT 2.60: 0.25%* |
| | Total Impurities: NMT 2.5% | 0.15% | ND | ND | 0.15% | 0.15% | 0.25% | 0.25% |
| Assay of Sodium Benzoate | 80.0%-110.0% of theoretical | 1) 99.5% 2) 100.1% Mean: 99.8% | 1) 100.6% 2) 100.6% Mean: 100.6% | 1) 100.2% 2) 100.0% Mean: 100.1% | 1) 101.7% 2) 102.8% Mean: 102.3% | 1) 102.2% 2) 102.2% Mean: 102.2% | 1) 102.5% 2) 102.0% Mean: 102.3% | 1) 102.2% 2) 102.3% Mean: 102.3% |
| pH | 4.5-5.5 | 5.04 | 4.96 | 4.98 | 5.0 | 5.0 | 5.0 | 5.0 |
| Osmolality | ≤400 mOsm/kg | 181 mOsm/kg | 185 mOsm/kg | 185 mOsm/kg | 182 mOsm/kg | 182 mOsm/kg | 185 mOsm/kg | 184 mOsm/kg |
| Specific Gravity | Report result | 1.0076 | NR | NR | NR | NR | NR | NR |
| Microbial Limits | TAMC: NMT $10^2$ cfu/mL | <10 cfu/mL | NR | NR | NR | NR | NR | NR |
| | TCYM: NMT $10^1$ cfu/mL | <10 cfu/mL | | | | | | |
| | E. Coli: Absent/mL | Absent/mL | | | | | | |
| | S. aureus: Absent/mL | Absent/mL | | | | | | |
| | P. aeruginosa: Absent/mL | Absent/mL | | | | | | |
| | Salmonella: Absent/10 mL | Absent/10 mL | | | | | | |
| | B. cepacia: Absent/mL | Absent/mL | | | | | | |

TABLE 5-continued

Stability of 250 mL at 40° C./60% RH

|  |  | Initial | 1 month | | 3 month | | 6 month | |
| --- | --- | --- | --- | --- | --- | --- | --- | --- |
|  |  |  | Upright | Inverted | Upright | Inverted | Upright | Inverted |
| AET | Meets acceptance criteria stated in USP<51> | Pass | NR | NR | NR | NR | NR | NR |
| Water Loss | Report result | NR | NR | NR | NR | NR | NR | NR |

*OOS66773

TABLE 6

Stability of 480 mL at 40° C./60% RH

|  |  | Initial | 1 month | | 3 month | | 6 month | |
| --- | --- | --- | --- | --- | --- | --- | --- | --- |
|  |  |  | Upright | Inverted | Upright | Inverted | Upright | Inverted |
| Date Samples Pulled |  | Apr. 4, 2013 | May 6, 2013 | May 6, 2013 | Jul. 9, 2013 | Jul. 9, 2013 | Oct. 4, 2013 | Oct. 4, 2013 |
| Appearance | Clear, colorless liquid | Complies | Complies | Complies | Complies | Complies | Complies | Complies |
| Appearance of Packaging | 480 mL, amber PET round bottle; white child resistant cap with induction seal. No visible damage to any of the components | Complies | Complies | Complies | Complies | Complies | Complies | Complies |
| Identification of Sotalol HCl by HPLC | Exhibits major peak for Sotalol; Retention time is the same as that of reference standard | Complies | NR | NR | NR | NR | NR | NR |
| Identification of Sotalol HCl by UV | The spectrum of the main peak in the sample chromatogram matches the spectrum of the main peak in the standard chromatogram | Complies | NR | NR | NR | NR | NR | NR |
| Assay for Sotalol HCl | 90.0%-110.0% of theoretical | 1) 101.0% 2) 102.1% Mean: 101.6% | 1) 100.8% 2) 100.6% Mean: 100.7% | 1) 100.9% 2) 101.0% Mean: 101.0% | 1) 101.2% 2) 100.9% Mean: 101.1% | 1) 101.6% 2) 101.8% Mean: 101.7% | 1) 102.7% 2) 102.5% Mean: 102.6% | 1) 102.2% 2) 101.9% Mean: 102.1% |
| Related Substances | Related Compound A: NMT 0.2% | ND | ND | ND | ND | ND | ND | ND |
|  | Related Compound B: NMT 0.2% | ND | ND | ND | ND | ND | ND | ND |
|  | Related Compound C: NMT 0.2% | ND | ND | ND | ND | ND | ND | ND |
|  | Unknown Impurities: NMT 0.1% | RRT 0.74: 0.14% RRT 2.12: <QL | ND | ND | RRT 2.42: 0.13%* | RRT 2.41: 0.13%* | RRT 2.58: 0.25%* | RRT 2.59: 0.24%* |
|  | Total Impurities: NMT 2.5% | 0.14% | ND | ND | 0.13% | 0.13% | 0.25% | 0.24% |
| Assay of Sodium Benzoate | 80.0%-110.0% of theoretical | 1) 100.0% 2) 99.9% Mean: 100.0% | 1) 101.2% 2) 100.6% Mean: 100.9% | 1) 100.8% 2) 100.4% Mean: 100.6% | 1) 102.4% 2) 102.3% Mean: 102.4% | 1) 102.7% 2) 102.1% Mean: 102.4% | 1) 102.3% 2) 102.3% Mean: 102.3% | 1) 101.9% 2) 100.7% Mean: 101.3% |
| pH | 4.5-5.5 | 5.06 | 4.96 | 4.95 | 5.0 | 5.0 | 5.0 | 5.0 |
| Osmolality | ≤400 mOsm/kg | 181 mOsm/kg | 185 mOsm/kg | 185 mOsm/kg | 182 mOsm/kg | 182 mOsm/kg | 186 mOsm/kg | 185 mOsm/kg |

TABLE 6-continued

Stability of 480 mL at 40° C./60% RH

|  |  |  | 1 month | | 3 month | | 6 month | |
| --- | --- | --- | --- | --- | --- | --- | --- | --- |
|  |  | Initial | Upright | Inverted | Upright | Inverted | Upright | Inverted |
| Specific Gravity | Report result | 1.0076 | NR | NR | NR | NR | NR | NR |
| Microbial Limits | TAMC: NMT $10^2$ cfu/mL | <10 cfu/mL | NR | NR | NR | NR | NR | NR |
|  | TCYM: NMT $10^1$ cfu/mL | <10 cfu/mL |  |  |  |  |  |  |
|  | E. Coli: Absent/mL | Absent/mL |  |  |  |  |  |  |
|  | S. aureus: Absent/mL | Absent/mL |  |  |  |  |  |  |
|  | P. aeruginosa: Absent/mL | Absent/mL |  |  |  |  |  |  |
|  | Salmonella: Absent/10 mL | Absent/10 mL |  |  |  |  |  |  |
|  | B. cepacia: Absent/mL | Absent/mL |  |  |  |  |  |  |
| AET | Meets acceptance criteria stated in USP<51> | Pass | NR | NR | NR | NR | NR | NR |
| Water Loss | Report result | NR | NR | NR | NR | NR | NR | NR |

*OOS66773

A photostability study was conducted under ICH light conditions on Sotalol Hydrochloride Oral Solution batch MFYN packaged in 250 mL and 480 mL packaging configuration. The samples were exposed to photostability conditions as described in ICH guideline Q1B "Stability Testing: Photostability Testing of New Drug Substances and Products, Option 2." The samples were exposed to light in the proposed commercial packaging and in the proposed commercial packaging wrapped in aluminum foil (control sample). The results are shown below:

Photostability Results for Sotalol Hydrochloride Oral Solution

| Test | Batch MHBV Light Exposed | Batch MHBV Light Control | Batch MHBP Light Exposed | Batch MHBP Light Control |
| --- | --- | --- | --- | --- |
| Assay for Sotalol HCL | 102.0% | 101.8% | 102.0% | 102.6% |
| Related Compound A (NMT 0.2%) | None Detected | None Detected | None Detected | None Detected |
| Related Compound B (NMT 0.2%) | None Detected | None Detected | None Detected | None Detected |
| Related Compound C (NMT 0.2%) | None Detected | None Detected | None Detected | None Detected |
| Total Impurities (NMT 0.2%) | 0.0 | 0.0 | 0.0 | 0.0 |
| Assay for Sodium Benzoate | 100.8% | 102.7% | 103.6% | 101.4% |
| pH | 5.0 | 5.0 | 5.0 | 5.0 |
| Osmolality (mOsm/kg) | 174 | 174 | 174 | 174 |
| Specific Gravity | 1.00645 | 1.00702 | 1.00676 | 1.00676 |

As the differences between the results for the light exposed and the control samples were insignificant, the Sotalol Hydrochloride Oral Solution, 5 mg/mL, was considered to be protected from light when contained in its primary packaging. The results met shelf life criteria for the individual tests. The Sotalol HCl assay results did not differ between the dark control and the light exposed samples. The assay for related substances demonstrated no significant degradation in both the dark control and light exposed samples, with no related substances results above the acceptance criteria of not more than (NMT) 0.1% individual unidentified impurities and no detected known related compounds. There were no impurity peaks detected in the samples above the reporting limit of 0.05%. Results for assay for preservative (sodium benzoate) did not differ between the dark control and light exposed samples. Osmolality, specific gravity, and pH results did not differ between the dark control and light exposed samples.

Results were within specification for all testing parameters (sotalol HCl assay, sodium benzoateassay, pH, osmolality, appearance, ID, water loss, and related substances A, B, & C). For unknown impurities, although stable at room temperature (25° C./60% RH) storage, drug product stability data show an additional impurity in the range RRT 2.57-2.81 that has presented above the ICH Q3B(R2) reporting threshold (0.1%) at accelerated storage conditions and at or near the 0.1% limit at the 30° C./65% RH condition. However, this impurity remains at or below the Quantification Limit at room temperature conditions.

Shelf-life Specifications and Analytical Tests

| Test | Limit | Method |
| --- | --- | --- |
| Appearance | Clear, colorless liquid | Visual inspection |
| Appearance of packaging | 480 mL, amber PET round bottle; white child resistant cap with induction seal. No visible damage to any of the components. 250 mL, amber PET round bottle; white child resistant cap with induction seal. No visible damage to any of the components. | Visual inspection |
| Identification of Sotalol HCl by HPLC (T = 0 only) | Exhibits major peak for Sotalol. Retention time is the same as that of reference standard. | CTMLP-3056 |
| Identification of Sotalol HCl by UV (T = 0 | The spectrum of the main peak in the sample chromatogram matches the spectrum of the | CTMLP-3056 |

Shelf-life Specifications and Analytical Tests

| Test | Limit | Method |
|---|---|---|
| only) | main peak in the standard chromatogram. | |
| Assay for Sotalol HCl | 90.0%-410.0% of theoretical | CTMLP-3056 |
| Related substances | Related Compound A: NMT 0.2%*<br>Related Compound B: NMT 0.2%<br>Related Compound C: NMT 0.2%*<br>Unidentified impurity: NMT 0.1%<br>Total impurities: NMT 2.5% | CTMLP-3056 |
| Assay for Sodium benzoate | 80.0%-110.0% of theoretical | CTMLP-3057 |
| pH | 4.5-5.5 | USP <791> |
| Osmolality | ≤400 mOsm/kg | USP <785> |
| Specific gravity (T = 0 only) | Report result | USP <841> Method 1 |

Analytical Tests

I) Identification of Sotalol HCl in Oral Solution by HPLC and UV (Study CTMLP-3056)

Equipment and Materials
HPLC system with UV detector and data acquisition
Balance, capable of accurately weighing to 0.1 mg
Sotalol Hydrochloride Reference Standard
Sotalol HCl Related Substance A, (RSI)
Sotalol HCl Related Substance B, (RS2)
Sotalol HCl Related Substance C, (RS3)
Column: Waters 1-1-Bondapack 300 mm×3.9 mm C18 (L 1)
Acetonitrile (HPLC Grade or equivalent)
Monobasic Potassium Phosphate (HPLC Grade or equivalent)
Miscellaneous glassware
0.45 μm nylon membrane filter
Deionized water
HPLC vial Procedure Preparation of Mobile Phase and Diluent—Make appropriate adjustment for larger or smaller final volume requirement.

1) Preparation of Phosphate Buffer Solution—For the preparation of one liter of Phosphate Buffer solution, dissolve 6.8 g of Monobasic Potassium Phosphate in 1000 ml D.I. water and mix well. Filter through 0.45 μm nylon membrane filter.
2) Preparation of Mobile Phase A—For the preparation of one liter of mobile phase, combine 950 ml of Phosphate Buffer solution with 50 ml of Acetonitrile. Mix well and degas. 3) Preparation of Mobile Phase B—100% acetonitrile, degas.
4) Preparation of Diluent—Combine 800 ml of D.I. water with 200 ml of Acetonitrile. Mix well.

Preparation of Standard Solution—Note: The working standard solution is stable up to 3 days at room temperature and 2-8° C.

1) Preparation of Working Standard Solution—Accurately weigh 20 mg of Sotalol Hydrochloride reference standard to a 100 ml volumetric flask. Dissolve and dilute to volume with diluent. Mix well. Concentration of Sotalol Hydrochloride: ~200 μg/ml
2) Preparation of Check Standard Solution—Same as Preparation of Working Standard Solution.
3) Preparation of Resolution Solution Note: The resolution solutions should be stored under refrigeration. The solution can be used as long as RSA, RSB and RSC peaks can be clearly identified in the resolution solution and all the system suitability parameters are met.

Accurately weigh and transfer 10±1 mg each of RS1 to RS3 reference material into three separate 500 ml volumetric flasks. Add approximately 350 ml of diluent into each flask to dissolve (sonicate 5 mins if necessary). Allow to cool to room temperature. Dilute to volume with diluent and mix well.

Accurately weigh 20 mg of Sotalol Hydrochloride reference standard into a 100 mL volumetric flask, add 5.0 ml of each known related substance stock standard solution. Dilute to volume with diluent and mix well.
Concentration of Sotalol HCl ~200 μg/ml.
Concentration of each known related substance ~1 μg/ml
Preparation of Sample Solution Note: Prepare sample solution in duplicate. The sample solutions are stable up to 3 days at room temperature and 2-8° C. Pipette 4.0 ml of a sample solution into a 100 ml volumetric flask. Dissolve and dilute to volume with diluent. Mix well. Filter a portion of the solution through a 0.45 pln Nylon syringe filters discarding the initial 3 ml of filtrate.
Concentration of Sotalol Hydrochloride: ~200 μg/ml Instrument Parameters
Column: Waters μ-Bondapack 300 mm×3.9 mm C18 (L 1)
Column Temperature: Ambient
Detection: UV@220 nm
Injection Volume: 35 μL
Flow Rate: 1.5 mL/min
Run Time: 45 minutes
Mobile Phase A: Phosphate Buffer: ACN=950:50 (v/v)
Mobile Phase B: 100% CAN Gradient Table:

| Time (Min) | A % | B % |
|---|---|---|
| 0.0 | 100 | 0 |
| 10.0 | 92 | 8 |
| 13.0 | 85 | 15 |
| 20.0 | 40 | 60 |
| 25.0 | 35 | 65 |
| 30.0 | 35 | 65 |
| 30.1 | 100 | 0 |
| 40.0 | 100 | 0 |

Injection Procedure
1) Make one injection of the diluent.
2) Make one injection of resolution solution
3) Make five consecutive injections of the working standard solution
4) Make one injections of the check standard solution
5) Make one injection of each sample solution
6) Make one injection of the working standard solution after every six sample solution injections and at the end of the sequence run The following system suitability criteria must be met.
The working standard solution will be consecutively injected five times. The RSD of the Sotalol Hydrochloride peak areas from the five consecutive injections of the working standard solution should be ≤2.0%.
Calculate the USP tailing factor, T, from, $$T = W_{0.05}/2f$$

Where, $W_{0.05}$ is the peak width of Sotalol Hydrochloride peak at 5% of the peak height from the baseline and f is the distance from the peak maximum to the leading edge of the peak. The USP tailing factor of Sotalol Hydrochloride peak in the first injection of the working standard solution should be ≤2.0.

The Number of Theoretical Plates per column, N, can be calculated as follows:

$$N=16(t/W)^2$$

Where t is the retention time of Sotalol Hydrochloride peak and W is the peak width of Sotalol Hydrochloride peak, obtained by extrapolating the relatively straight sides of peak to the base line. The Number of Theoretical Plates per column for Sotalol Hydrochloride peak in the first injection of the Working standard solution should be ≥2000.

Calculate the resolution factor (R) between all successive and adjacent peaks from the resolution solution as follows:

$$R = \frac{2(t_{n+1} - t_n)}{W_{n+1} + W_n}$$

Where,
$t_n$=Retention time of peak n
$t_{n+1}$=Retention time of peak n+1
$W_n$=Peak width of peak n
$W_{n+1}$=Peak width of peak n+1

The resolution factor between all successive and adjacent peaks in the resolution solution should be ≥2.0.

Make one injection of the check standard solution into HPLC system for analysis. Calculate the % recovery of Sotalol Hydrochloride in the check standard as follows:

$$\% \text{ Recovery}=(A_{CK}/Wt_{CK})\times(Wt_{WSTD}/A_{WSTD})\times100\%$$

Where,
$A_{CK}$=Peak area of Sotalol Hydrochloride from the check standard solution
$A_{WSTD}$=Average peak area of Sotalol Hydrochloride from five injections of the working standard solution
$Wt_{CK}$=Weight of Sotalol Hydrochloride in the preparation of the check standard solution
$Wt_{WSTD}$=Weight of Sotalol Hydrochloride used in the preparation of the working standard solution The % recovery of Sotalol Hydrochloride of the check standard solution should be within 98.0% to 102.0%.

System Drift

Make one injection of the working standard solution after injection of every six sample injections and at the end of the sequence run. Calculate the % recovery of Sotalol Hydrochloride from each system drift injections as follows:

$$\% \text{ Recovery}=(A_{SCK}/A_{WSTD})\times100$$

Where,
$A_{SCK}$=Peak area of Sotalol Hydrochloride from the system drift injection of the working standard solution
$A_{WSTD}$=Average peak area of Sotalol Hydrochloride from the first five system suitability injections of the working standard solution For system drift, the % recovery of Sotalol Hydrochloride from every system drift injection throughout the sequence run should be within 98.0% to 102.0%.

Calculation and Results

% LC of Sotalol HCl can be calculated as follows:

$$\% LC=(A_{spl}/A_{std})\times W_{std}\times P_{std}\times(DF_{spl}/DF_{std})\times(1/V\times LC)\times100\%$$

Impurities can be calculated as follows:

$$\% RS=(A_{RS}/A_{std})\times W_{std}\times P_{std}\times(DF_{spl}/DF_{std})\times(RRF/V\times LC)\times100\%$$

Where:
$A_{spl}$=Peak Area of Sotalol Hydrochloride obtained from Sample Preparation
$A_{std}$=Average Peak Area of Sotalol Hydrochloride obtained from five injections of Working Standard Solution
$W_{std}$=Weight of Sotalol Hydrochloride Reference Standard (mg)
$P_{std}$=Potency of Sotalol Hydrochloride Reference Standard
$DF_{std}$=Dilution Factor of the Working Standard Preparation
$DF_{spl}$=Dilution Factor of the Sample Preparation
LC=Label Claim of Sotalol Hydrochloride
V=Sample Volume (4.0 ml)
RRF=Relative Response Factor (Known Impurities of RSA=1.33; RSB=0.70; RSC=0.99; all unknown: 1.00)

Report the % LC of Sotalol HCl to one decimal place
Report % Related substances to two decimal places>0.05%.

The DL/QL and RRF values are listed below:

| Related Substance | DL | QL | RRF |
| --- | --- | --- | --- |
| Unknown related substance (based on Sotalol HCl) | 0.02% | 0.05% | 1.0 |
| $RS_A$ | 0.02% | 0.05% | 1.33 |
| $RS_B$ | 0.02% | 0.05% | 0.7 |
| $RS_C$ | 0.02% | 0.05% | .99 |

If the related substance is present below the QL but above DL report as <QL.

If the related substance is present at <DL report as not detected

II) Assay for Sodium Benzoate (Study CTMLP-3057)
Equipment and Materials
HPLC system with UV detector and data acquisition
Balance, capable of accurately weighing to 0.1 mg
pH meter
Sodium Benzoate Reference Standard
Column: Agilent Zorbax C18, 5 μm 4.6 mm×250 mm
HPLC vial
Acetonitrile (HPLC Grade or equivalent)
Ammonium Acetate (HPLC Grade or equivalent)
Glacial Acetic Acid (HPLC Grade or equivalent)
Miscellaneous glassware
0.45 um nylon membrane filter
Deionized water
Procedure
1) Preparation of Mobile Phase and Diluent—Make appropriate adjustment for larger or smaller final volume requirement.
2) Preparation of Acetate Buffer Solution—For the preparation of one liter of Acetate Buffer Solution, dissolve 0.30 g of Ammonium Acetate in about 900 ml of 0.1. water. Adjust the pH to 4.2 to 0.05 with Glacial Acetic Acid and dilute with D.I. water to 1000 ml, and mix well. Filter through 0.45 μg nylon membrane filter.
3) Preparation of Mobile Phase—For the preparation of one liter of mobile phase, combine 900 ml of Acetate Buffer (pH=4.2) with 125 ml of Acetonitrile. Mix well and degas before use.
4) Preparation of Diluent—The same preparation as Preparation of Mobile Phase.
Preparation of Standard Solution—
1) Preparation of Stock Standard Solution
   Accurately weigh 50 mg of Sodium Benzoate reference standard, and transfer to a 50 ml volumetric flask.

Dissolve and dilute to volume with diluent. Mix well. Concentration of Sodium Benzoate: ~1000 µg/ml.

2) Preparation of Working Standard Solution

Note: The working standard solution is stable up to 4 days at room temperature and 2-8° C. Pipette 5.0 ml of the stock standard solution to a 100 ml volumetric flask. Dilute to volume with diluent and mix. Concentration of Sodium Benzoate: ~50 µg/ml 3) Preparation of Check Standard Solution Repeat section Preparation of Stock Standard Solution and Preparation of Working Standard Solution.

4) Preparation of Sample Solution

Note: Prepare sample solution in duplicate. The sample solution is stable up to 3 days at room temperature and 2-8° C.

For sample containing 2.5 mg/ml Sodium Benzoate Pipette 10.0 ml of a sample solution into a 100 ml volumetric flask. Dissolve and dilute to volume with diluent. Mix well. Pipette 10.0 ml of the solution to a 50 mL volumetric flask and dilute to volume with diluent. Mix well.

Concentration of Sodium Benzoate: ~50 µg/mL

For sample containing 2.0 mgl ml Sodium Benzoate Pipette 12.0 ml of a sample solution Into a 100 ml volumetric flask. Dissolve and dilute to volume with diluent. Mix well. Pipette 10.0 ml of the solution to a 50 mL volumectric flask and dilute to volume with diluent. Mix well.

Concentration of Sodium Benzoate: ~48 µg/ml

Instrument Parameters

Column: Agilent Zorbax C18, 4.6 mm×250 mm,
Column Temperature: Ambient
Detection: UV@225 nm
Injection Volume: 5~
Flow Rate: 1.5 mL/min
RunTime: 22 minutes
Mobile Phase: Acetate Buffer: ACN=900:125 (v/v)

Injection Procedure

1) Make one injection of the diluent.
2) Make five consecutive injections of the working standard solution
3) Make one injections of the check standard solution
4) Make one injection of each sample solution
5) Make one injection of the working standard solution after every six sample solution Injections and at the end of the sequence run The following system suitability criteria must be met.

The working standard solution will be consecutively injected five times. The RSD of the Sodium Benzoate peak areas from the five consecutive injections of the working standard solution should be ≤2.0%.

Calculate the USP tailing factor, T, from, $$T = W_{0.05}/2f$$

Where, $W_{0.05}$ is the peak width of Sodium Benzoate peak at 5% of the peak height from the baseline and f is the distance from the peak maximum to the leading edge of the peak. The USP tailing factor of Sodium Benzoate peak in the first injection of the working standard solution should be ≤2.0.

The Number of Theoretical Plates per column, N, can be calculated as follows:

$$N = 16(t/W)^2$$

Where t is the retention time of Sodium Benzoate peak and W is the peak width of Sodium Benzoate peak, obtained by extrapolating the relatively straight sides of peak to the base line. The Number of Theoretical Plates per column for Sodium Benzoate peak in the first injection of the Working standard solution should be ≥2000.

Make one injection of the check standard solution into HPLC system for analysis. Calculate the % recovery of Sodium Benzoate in the check standard as follows.

$$\% \text{ Recovery} = (A_{CK}/Wt_{CK}) \times (Wt_{WSTD}/A_{WSTD}) \times 100\%$$

Where, $A_{CK}$=Peak area of Sodium Benzoate from the check standard solution $A_{WSTD}$=Average peak area of Sodium Benzoate from five injections of the working standard solution $Wt_{CK}$=Weight of Sodium Benzoate in the preparation of the check standard solution $Wt_{WSTD}$=Weight of Sodium Benzoate used in the preparation of the working standard solution The % recovery of Sodium Benzoate of the check standard solution should be within 98.0% to 102.0%.

System Drift

Make one injection of the working standard solution after injection of every six sample injections and at the end of the sequence run. Calculate the % recovery of Sodium Benzoate from each system drift injections as follows:

$$\% \text{ Recovery} = (A_{SCK}/A_{WSTD}) \times 100$$

Where, $A_{SCK}$=Peak area of Sodium Benzoate from the system drift injection of the working standard solution $A_{WSTD}$=Average peak area of Sodium Benzoate from the first five system suitability injections of the working standard solution For system drift, the % recovery of Sodium Benzoate from every system drift injection throughout the sequence run should be within 98.0% to 102.0%.

Calculation and Results

The results can be calculated as follows:

$$\% \text{ Sodium Benzoate} = (A_{spl}/A_{std}) \times W_{std} \times P_{std} \times (DF_{spl}/DF_{std}) \times (1/LC) \times 100\%$$

Where:

$A_{SCK}$=Peak Area of Sodium Benzoate obtained from Sample Preparation $A_{std}$=Average Peak Area of Sodium Benzoate obtained from five injections of Working Standard Solution $W_{std}$=Weight of Sodium Benzoate Reference Standard (mg)

$P_{std}$=Potency of Sodium Benzoate Reference Standard $DF_{std}$=Dilution Factor of the Working Standard Preparation $DF_{spl}$=Dilution Factor of the Sample Preparation LC=Label Claim of Sodium Benzoate (2.5 mg/mL or 2.0 mg/mL)

Report result to one decimal

We claim:

1. An oral solution comprising sotalol hydrochloride, wherein the solution is homogenous.

2. The oral solution of claim 1, wherein the solution is free of polymers.

3. The oral solution of claim 1, wherein the solution is stable for greater than four months.

4. The oral solution of claim 1, wherein the solution is stable for greater than twelve months.

5. The oral solution of claim 1, wherein the solution has a pH between about 3 and about 7.

6. The oral solution of claim 1, wherein the solution has an osmolality in the range of about 20 mOsm/kg to about 400 mOsm/kg.

7. The oral solution of claim 1, wherein sotalol hydrochloride is present in an amount of about 5 mg/mL or about 0.5% by weight.

8. The oral solution of claim 1, wherein the sotalol hydrochloride is present in an amount from about 0.2% to about 0.8% by weight.

9. The oral solution of claim 1, further comprising an excipient selected from the group consisting of buffering substances, preservatives, high potency sweeteners and flavoring agents, or combinations thereof.

10. The oral solution of claim 9, wherein the buffering substance is sodium citrate or citric acid, alone or in combination.

11. The oral solution of claim 9, wherein the preservative is sodium benzoate.

12. The oral solution of claim 9, wherein the high potency sweetener is sucralose.

13. The oral solution of claim 9, wherein the flavoring agent is artificial grape flavor.

14. An oral solution comprising water in an amount of about 95% to about 99% by weight, sotalol hydrochloride in an amount from about 0.2% to about 8% by weight, at least one buffering substance, at least one preservative, and optionally, at least one high potency sweetener and at least one flavor ingredient.

15. The oral solution of claim 14, wherein the solution is free of polymers.

16. The oral solution of claim 14, wherein the solution is stable for greater than four months.

17. The oral solution of claim 14, wherein the solution is stable for greater than eight months.

18. The oral solution of claim 14, wherein the solution is stable for greater than twelve months.

19. The oral solution of claim 14, wherein the solution has an osmolality in the range of about 200 mOsm/kg to about 250 mOsm/kg.

* * * * *